United States Patent [19]

Doi et al.

[11] Patent Number: 4,977,211

[45] Date of Patent: Dec. 11, 1990

[54] WATER-ABSORPTIVE RESIN COMPOSITION

[75] Inventors: Shuhei Doi; Shunichi Ohnishi, both of Mie, Japan

[73] Assignee: Mitsubishi Pertochemical Co., Ltd., Tokyo, Japan

[21] Appl. No.: 225,733

[22] Filed: Jul. 29, 1988

[30] Foreign Application Priority Data

Jul. 30, 1987 [JP] Japan .................... 62-191096

[51] Int. Cl.$^5$ .................... C08L 3/04; C08L 23/16; C08L 23/04; C08L 23/10
[52] U.S. Cl. .................... 525/54.31; 525/54.26; 525/54.3; 525/54.32; 525/57; 525/196; 525/201; 525/207; 525/221; 527/314
[58] Field of Search .................... 525/54.31, 196, 201, 525/221, 54.3, 54.26, 57, 54.32, 207; 527/314

[56] References Cited

U.S. PATENT DOCUMENTS

| | | | |
|---|---|---|---|
| 4,472,545 | 9/1984 | Coughlin et al. | 524/524 |
| 4,480,061 | 10/1984 | Couglin et al. | 525/222 |
| 4,590,227 | 5/1986 | Nakamura et al. | 525/57 |
| 4,728,692 | 3/1988 | Sezaki et al. | 525/196 |

FOREIGN PATENT DOCUMENTS

| | | |
|---|---|---|
| 57-190065 | 11/1982 | Japan . |
| 62-172044 | 7/1987 | Japan . |
| 62-190239 | 8/1987 | Japan . |

*Primary Examiner*—Carman J. Seccuro
*Attorney, Agent, or Firm*—Oblon, Spivak, McClelland, Maier & Neustadt

[57] ABSTRACT

A water-absorptive resin composition which comprises (A) 5 to 95% by weight of a water-absorptive resin and 95 to 5% by weight of (B) a polyolefin resin and (C) an ethylene/α-olefin copolymer rubber, based on the total contents of said components (A), (B) and (C), wherein the content of said component (C) amounts to 20 to 80% by weight based on the total contents of said components (B) and (C) is disclosed. This water-absorptive resin composition is moldable and has an excellent water absorption property and an excellent water-absorptive resin retention characteristic after absorbing water.

7 Claims, No Drawings

WATER-ABSORPTIVE RESIN COMPOSITION

FIELD OF THE INVENTION

This invention relates to a moldable water-absorptive resin composition which has an excellent water absorption property and an excellent water-absorptive resin retention characteristic after absorbing water.

BACKGROUND OF THE INVENTION

Water-absorptive resins have been widely applied to, for example, sanitary absorbent materials such as paper diaper and sanitary napkin, agricultural water retention materials and industrial materials. Examples of these conventional water-absorptive resins include starch derivatives such as alkali metal salts of starch/acrylic acid graft copolymer, saponified starch/ acrylonitrile graft copolymer and saponified starch/ acrylamide graft copolymer; cellulose derivatives such as carboxymethyl cellulose, saponified cellulose/ acrylonitrile graft copolymer and alkali metal salts of cellulose/acrylic acid graft copolymer; polyacrylic acid derivatives such as alkali metal polyacrylates; and polyvinyl alcohol derivatives such as alkali metal salts of polyvinyl alcohol/acrylic acid graft copolymer and polyvinyl alcohol/maleic anhydride graft copolymer. Each of these resins is formulated into a crosslinked powder in order to achieve a shape-retention characteristic after absorbing water.

Recently the range of the application of these water-absorptive resins has been more and more increasing and it is required to formulate these resins not only into a powder but also into various forms including film, sheet and fiber. However, every conventional water-absorptive resin is a crosslinked material and thus has a poor thermoplasticity, which makes it significantly difficult to mold the same into a film, a sheet or fibers.

On the other hand, it has been attempted to mold a conventional water-absorptive resin into a film or fibers by, for example, employing a composition of a water-absorptive resin with a polyolefin resin such as polyethylene, ethylene/vinyl acetate copolymer, ethylene/acrylic acid copolymer or ethylene/propylene copolymer or rubber (cf. Japanese Laid-Open Patent Application Nos. 75747/76, 33032/81 and 145151/82). However, the composition thus obtained has some disadvantages such that the water absorption ratio is lowered and that the water-absorptive resin is significantly eliminated after absorbing water, though the aimed moldability is achieved.

SUMMARY OF THE INVENTION

The present inventors have found that a composition comprising a water-absorptive resin in combination with a polyolefin resin and an ethylene/ a-olefin copolymer rubber not only shows an excellent moldability, but also exhibits an excellent water absorption property and an excellent water-absorptive resin retention characteristic after absorbing water (i.e., no elimination of the water-absorptive resin after absorbing water), and succeeded in accomplishing the present invention. Accordingly, an object of the present invention is to provide a moldable water-absorptive resin composition which has an excellent water absorption property and an excellent water-absorptive resin retention characteristic after absorbing water.

The water-absorptive resin composition of the present invention comprises (A) 5 to 95% by weight of a water-absorptive resin and 95 to 5% by weight of (B) a polyolefin resin and (C) an ethylene/a-olefin copolymer rubber, based on the total content of the components (A), (B) and (C), wherein the content of the component (C) amounts to 20 to 80% by weight based on the total content of the components (B) and (C).

DETAILED DESCRIPTION OF THE INVENTION

Examples of the water-absorptive resin to be employed as the component (A) include starch derivatives such as alkali metal salts of starch/(meth)acrylic acid graft copolymer, hydrolyzed starch/(meth)acrylates graft copolymer, saponified starch/(meth)acrylonitrile graft copolymer and saponified starch/(meth)acrylamide graft copolymer; cellulose derivatives such as carboxymethyl cellulose, saponified cellulose/(meth)acrylonitrile graft copolymer and alkali metal salts of cellulose/(meth)acrylic acid graft copolymer; polyacrylic acid derivatives such as alkali metal poly(meth)acrylates and alkali metal salts of (meth)acrylic acid/(meth)acrylamide copolymer; polyvinyl alcohol derivatives such as alkali metal salts of polyvinyl alcohol/(meth)acrylic acid graft copolymer and polyvinyl alcohol/maleic anhydride graft copolymer; alkali metal salts of vinyl acetate/(meth)acrylic acid copolymer and isobutylene/maleic anhydride copolymer. Preferred examples of the water-absorptive resin to be employed as the component (A) include alkali metal salts of starch/acrylic acid graft copolymer and alkali metal polyacrylates. It is preferable that these resins are crosslinked.

Typical examples of the polyolefin resin to be employed as the component (B) include polyethylene, polypropylene, ethylene/propylene copolymer, ethylene/ 1-butene copolymer, propylene/1-butene copolymer, ethylene/vinyl acetate copolymer, ethylene/(meth)acrylic acid copolymer and ethylene/(meth)acrylates copolymer. Preferred examples of the polyolefin resin to be employed as the component (B) include ethylene/vinyl acetate copolymer and polypropylene.

Examples of the ethylene/a-olefin copolymer rubber to be employed as the component (C) include ethylene/propylene copolymer rubber, ethylene/1-butene copolymer rubber and a copolymer rubber obtained by copolymerization of the monomers for the aforesaid rubber with an unconjugated diene such as dicyclopentadiene, 1,4-hexadiene or ethylidenenorbornene. Preferred examples of the ethylene/a-olefin copolymer rubber to be employed as the component (C) include ethylene/propylene copolymer rubber. It is preferable that the component (C) contains 70 to 85% by weight of ethylene units.

The composition of the present invention comprises 5 to 95% by weight, preferably 20 to 80% by weight, of the component (A) and 95 to 5% by weight, preferably 80 to 20% by weight, of the components (B) and (C), based on the total content of the components (A), (B) and (C). When the content of the component (A) is less than 5% by weight, there is no advantage to use the composition as a water-absorptive material because of a poor water absorption property of the composition. When it exceeds 95% by weight, on the other hand, the composition has a poor moldability.

The ratio of these components may be varied within the range as specified above. Generally, it is preferable to increase the content of the component (A) in order to achieve an excellent water absorption property while it is preferable to increase the content of the components (B) and (C) in order to achieve an excellent moldability.

In the composition of the present invention, the content of the component (C) amounts to 20 to 80% by weight based on the total content of the components (B) and (C). when the content of the component (C) departs from this range, neither a water absorption property nor a water-absorptive resin retention characteristic can be improved remarkably. It is preferable that the content of the component (C) amounts to 30 to 70% by weight.

The water-absorptive resin composition of the present invention may be produced by melt-kneading the components (A), (B) and (C) as described above optionally together with various additives such as petroleum resin, wax, stabilizer, antistatic agent, UV absorber, lubricant or inorganic filler by using a conventional kneader such as a biaxial kneader, for example, roll, Banbury mixer, Brabender Plastograph, CIM or FCM or a monoaxial extruder at a temperature higher than the melting point of the component (B).

Subsequently the water-absorptive resin composition of the present invention can be molded into a form suitable for its final use. The molded products may be subjected to a secondary molding treatment such as foaming or orientation. That is to say, the composition can be molded alone into a film, a sheet, fibers or other products. Alternatively, it may be molded together with other material(s) into a laminated film, sheet or other products. The fibers may be woven into cloth. These products thus obtained are widely available as, for example, packaging materials for foods or drugs, agricultural materials, building materials for preventing dropwise condensation or for interior uses, civil engineering materials for waterstop, sanitary materials, oil/water separating materials or antistatic materials.

The water-absorptive resin composition of the present invention, which comprises a polyolefin resin together with an ethylene/α-olefin copolymer rubber, exhibits not only a moldability but also an excellent water absorption property and an excellent water-absorptive resin retention characteristic after absorbing water.

The following examples and comparative examples will serve to illustrate the present invention in more detail, but they are not to be construed as limiting the present invention in any manner.

In the following examples and comparative examples, each water absorption ratio and water-absorptive resin retention ratio were determined by the following methods.

Water Absorption Ratio

A sample of a water-absorptive resin composition weighing approximately 1 g and approximately 1 l of pure water were introduced into a 1 l beaker and allowed to stand therein at 25° C. for 24 hours to thereby allow the sample to sufficiently swell. The sample was drained on an 8-mesh sieve and moisture adhering to its surface was wiped with a paper filter. Then the sample was weighed. The water absorption ratio was determined according to the following equation.

$$\text{Water absorption ratio (\%)} = \frac{\text{Weight of sample after absorbing water (g)} - \text{Weight of sample before absorbing water (g)}}{\text{Weight of sample before absorbing water (g)}} \times 100$$

Water-Absorptive Resin Retention Ratio

The sample used in the determination of the water absorption ratio was vacuum dried at 100° C. for 24 hours and then allowed to stand in a desiccator until it reached room temperature. Then it was weighed. The difference between the weight of the sample before immersing in water and that after the vacuum drying was regarded as the dry weight loss. Thus, the water-absorptive resin retention ratio was determined according to the following equation.

$$\text{Water-absorptive resin retention ratio (\%)} = \frac{\text{Weight of water-absorptive resin in sample before immersing in water (g)} - \text{Dry weight loss of sample (g)}}{\text{Weight of water-absorptive resin in sample before immersing in water (g)}} \times 100$$

EXAMPLE 1

40% by weight of sodium polyacrylate (Diawet; manufactured by Mitsubishi Petrochemical Co., Ltd., average particle size: 50 μm) employed as the component (A), 45% by weight of ethylene/vinyl acetate copolymer (Mitsubishi EVA X700; manufactured by Mitsubishi Petrochemical Co., Ltd., vinyl acetate content: 33% by weight, melt index: 30 g/10 min) employed as the component (B), and 15% by weight of ethylene/propylene copolymer rubber (EP02P; manufactured by Japan Synthetic Rubber Co., Ltd., ethylene content: 74% by weight) employed as the component (C), based on the total content of the components (A), (B) and (C), were mixed together in a Henschel mixer for 3 minutes. The resulting mixture was melt-kneaded by using a Banbury mixer at 150° C. for 10 minutes to thereby give a water-absorptive resin composition.

The obtained composition was press molded into a sheet of 0.1 mm in thickness and the water absorption ratio and water-absorptive resin retention ratio thereof were determined. The following table shows the results.

EXAMPLES 2 TO 5 AND COMPARATIVE EXAMPLES 1 TO 4

The procedure of Example 1 was repeated except the composition of the components (A), (B) and (C) was varied as shown in the following table.

EXAMPLE 6

The procedure of Example 1 was repeated except 40% by weight of a sodium salt of starch/acrylic acid graft copolymer (Sunwet IM300MPS; manufactured by Sanyo Chemical Industries, Ltd., average particle size: 30 μm), 45% by weight of polypropylene (Mitsubishi Polypro MA3; manufactured by Mitsubishi Petrochemical Co., Ltd., melt index: 10 g/10 min) and 15% by weight of ethylene/ propylene copolymer rubber (EP11; manufactured by Japan Synthetic Rubber Co., Ltd., ethylene content: 51% by weight) were employed as the components (A), (B) and (C), respectively, the total content of the components (A), (B) and (C) being 100% by weight, to thereby give a water-absorptive resin composition.

EXAMPLES 7 AND 8 AND COMPARATIVE EXAMPLES 5 AND 6

The procedure of Example 6 was repeated except that the compositions of the components (A), (B) and (C) were varied as shown in the following table.

While the invention has been described in detail and with reference to specific embodiments thereof, it will be apparent to one skilled in the art that various changes and modifications can be made therein without departing from the spirit and scope thereof.

What is claimed is:

1. A water-absorptive resin composition, which comprises:
   (A) 5 to 95% by weight of a water-absorptive resin selected from the group consisting of an alkali metal polyacrylate and an alkali metal salt of starc-

|  | Composition | | | Content | | | | Water Absorption Ratio (% by weight) | Water-absorptive Resin Retention Ratio (% by weight) |
|---|---|---|---|---|---|---|---|---|---|
|  | Component (A) | Component (B) | Component (C) | (A)/(A)+(B)+(C) (% by weight) | (B)/(A)+(B)+(C) (% by weight) | (C)/(A)+(B)+(C) (% by weight) | (C)/(B)+(C) (% by weight) | | |
| Example 1 | Sodium polyacrylate | Ethylene/vinyl acetate copolymer | Ethylene/propylene copolymer rubber | 40 | 45 | 15 | 25 | 1,500 | 65 |
| Example 2 | Sodium polyacrylate | Ethylene/vinyl acetate copolymer | Ethylene/propylene copolymer rubber | " | 30 | 30 | 50 | 5,500 | 70 |
| Example 3 | Sodium polyacrylate | Ethylene/vinyl acetate copolymer | Ethylene/propylene copolymer rubber | " | 15 | 45 | 75 | 610 | 60 |
| Comparative Example 1 | Sodium polyacrylate | Ethylene/vinyl acetate copolymer | Ethylene/propylene copolymer rubber | " | 60 | 0 | 0 | 400 | 20 |
| Comparative Example 2 | Sodium polyacrylate | Ethylene/vinyl acetate copolymer | Ethylene/propylene copolymer rubber | " | 0 | 60 | 100 | 120 | 5 |
| Example 4 | Sodium polyacrylate | Ethylene/vinyl acetate copolymer | Ethylene/propylene copolymer rubber | 20 | 40 | 40 | 50 | 1,430 | 70 |
| Comparatvie Example 3 | Sodium polyacrylate | Ethylene/vinyl acetate copolymer | Ethylene/propylene copolymer rubber | " | 80 | 0 | 0 | 150 | 15 |
| Example 5 | Sodium polyacrylate | Ethylene/vinyl acetate copolymer | Ethylene/propylene copolymer rubber | 80 | 10 | 10 | 50 | 20,000 | 80 |
| Comparative Example 4 | Sodium polyacrylate | Ethylene/vinyl acetate copolymer | Ethylene/propylene copolymer rubber | " | 20 | 0 | 0 | 8,000 | 30 |
| Example 6 | Sodium salt of starch/acrylic acid graft copolymer | Polypropylene | Ethylene/propylene copolymer rubber | 40 | 45 | 15 | 25 | 320 | 55 |
| Example 7 | Sodium salt of starch/acrylic acid graft copolymer | Polypropylene | Ethylene/propylene copolymer rubber | " | 30 | 30 | 50 | 820 | 75 |
| Example 8 | Sodium salt of starch/acrylic acid graft copolymer | Polypropylene | Ethylene/propylene copolymer rubber | " | 15 | 45 | 75 | 250 | 60 |
| Comparative Example 5 | Sodium salt of starch/acrylic acid graft copolymer | Polypropylene | Ethylene/propylene copolymer rubber | " | 60 | 0 | 0 | 100 | 15 |
| Comparative Example 6 | Sodium salt of starch/acrylic acid graft copolymer | Polypropylene | Ethylene/propylene copolymer rubber | " | 0 | 60 | 100 | 90 | 5 | h/acrylic acid graft copolymer and 95 to 5% by weight of (B) a polyolefin resin and (C) an ethylene/a-olefin copolymer rubber, based on the total contents of said components (A), (B) and (C), wherein the content of said component (C) amounts to 20 to 80% by weight based on the total contents of said components (B) and (C).

2. A water-absorptive resin composition as claimed in claim 1, wherein said polyolefin resin employed as the component (B) is ethylene/vinyl acetate copolymer.

3. A water-absorptive resin composition as claimed in claim 1, wherein said polyolefin resin employed as the component (B) is polypropylene.

4. A water-absorptive resin composition as claimed in claim 1, wherein said ethylene/a-olefin copolymer rubber employed as the component (C) is ethylene/propylene copolymer rubber.

5. A water-absorptive resin composition as claimed in claim 1, wherein said ethylene/a-olefin copolymer rubber employed as the component (C) contains 70 to 85% by weight of ethylene units.

6. A water-absorptive resin composition as claimed in claim 1, wherein the content of said component (A) amounts to 20 to 80% by weight based on the total contents of said components (A), (B) and (C).

7. A water-absorptive resin composition as claimed in claim 1, wherein the content of said component (C) amounts to 30 to 70% by weight based on the total contents of said components (B) and (C).

* * * * *